United States Patent [19]

Chockalingam et al.

[11] Patent Number: 5,399,747
[45] Date of Patent: Mar. 21, 1995

[54] PROCESS FOR PREPARING CARBOXYLIC ACIDS BY CARBONYLATION OF ETHERS AND THIOETHERS

[75] Inventors: Kannappan Chockalingam; Tse-Chong Wu, both of Baton Rouge, La.

[73] Assignee: Albemarle Corporation, Richmond, Va.

[21] Appl. No.: 187,027

[22] Filed: Jan. 27, 1994

[51] Int. Cl.6 .......................................... C07C 51/10
[52] U.S. Cl. ........................... 562/406; 560/9; 560/15; 560/20; 560/21; 560/51; 560/55; 560/56; 560/60; 560/100; 560/105
[58] Field of Search ............. 562/406; 560/9, 15, 560/20, 21, 51, 55, 56, 60, 100, 105

[56] References Cited

U.S. PATENT DOCUMENTS

| | | | |
|---|---|---|---|
| 2,913,489 | 11/1959 | Benedictis | 562/406 |
| 3,769,324 | 10/1973 | Paulik | 562/406 |
| 5,166,418 | 11/1992 | Hendricks | 562/406 |
| 5,315,030 | 5/1994 | Chochalingam | 560/105 |

*Primary Examiner*—Michael L. Shippen
*Attorney, Agent, or Firm*—Richard J. Hammond

[57] ABSTRACT

A new process for preparing aryl-substituted aliphatic carboxylic acids is provided. Aryl-substituted aliphatic ether or thioether compound is reacted with carbon monoxide in aqueous conditions at a temperature between about 25° C. and about 200° C. An acid such as hydrochloric acid may be added. As catalyst, a mixture of palladium or a palladium compound and a copper compound with at least one acid-stable ligand are present.

10 Claims, No Drawings

PROCESS FOR PREPARING CARBOXYLIC ACIDS BY CARBONYLATION OF ETHERS AND THIOETHERS

TECHNICAL FIELD

This invention relates to a process for preparing aryl-substituted aliphatic carboxylic acids or the esters thereof.

BACKGROUND OF THE INVENTION

Among the processes known for preparing ibuprofen is that of European Patent Application 284,310 (Hoechst Celanese, published September, 1988), which teaches that ibuprofen can be prepared by carboxylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. Pat. No. 4,536,595, issued August, 1985) teach the preparation of alkaline salts of certain alphaarylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270–1271, discloses the alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and *J. Am. Chem. Soc.*, 112, 2803–2804 (1990).

THE INVENTION

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl (for the purposes of this definition, "alkyl" is also "aliphatic");

"cycloakyl" means cyclic alkyl having 3 to 7 carbon atoms and includes cyclopropyl, cyclobutyl, cyclopentyl, cyclohexyl, and cycloheptyl;

"substituted aryl" means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, aryloxy including phenoxy and phenoxy substituted with halo, alkyl, alkoxy and the like, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, and 2,2,3,3-tetrafluoropropyl;

"alkyl-substituted cycloalkyl" means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, and 6-cyclohexylhexyl;

"alkylthio" means a divalent sulfur with alkyl occupying one of the valencies and includes the groups methylthio, ethylthio, propylthio, butylthio, pentylthio, hexylthio, and octylthio;

"heteroaryl" means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl, and indolyl;

"substituted heteroaryl" means 5 to 10 membered mono- or fused-heteroaromatic ring which has at least one heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl;

"aroyl" means benzoyl or naphthoyl;

"substituted aroyl" means benzoyl or naphthoyl substituted by at least one substituent selected from the group consisting of halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl, benzimidazolylcarbonyl;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl.

The present invention embraces any racemates and individual optical isomers thereof of the compounds of the following formula (I) having a chiral carbon atom.

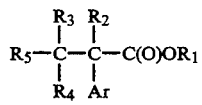

where Ar, $R_1$, $R_2$, $R_3$, $R_4$ and $R_5$ are subsequently defined.

In accordance with the present invention, aryl-substituted aliphatic carboxylic acids or the esters thereof are prepared by carbonylating an aryl-substituted, aliphatic ether or thioether with carbon monoxide in a neutral or acidic medium containing at least 1 mol of water per mol of the ether or thioether at a temperature of between about 25° C. and about 200° C. and a carbon monoxide pressure of at least about one atmosphere in the presence of a) palladium metal or a compound of palladium in which the palladium has a valence of 1 or 2 or b) a mixture of (i) palladium(O) or a palladium compound in which the palladium has a valence of 1 or 2 and (ii) a copper compound having a valence of 1 or 2 and c) at least one acid-stable ligand.

The ether or thioether which is catalytically carbonylated in the practice of this invention has the formula:

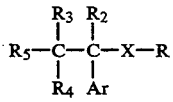

where X is oxygen or sulfur and R is alkyl or substituted or unsubstituted aryl, Ar is unsubstituted or substituted aryl and $R_2$, $R_3$, $R_4$ and $R_5$ are hydrogen, alkyl, cycloalkyl, substituted or unsubstituted aryl, alkoxy, alkylthio, substituted or unsubstituted heteroaryl, alkanoyl, substituted or unsubstituted aroyl, substituted or unsubstituted heteroarylcarbonyl, trifluoromethyl or halo.

Preferably, in the compounds of formula II, X is oxygen, R is alkyl, Ar is unsubstituted or substituted aryl, $R_2$, $R_3$, $R_4$ and $R_5$ are hydrogen, methyl or ethyl, substituted or unsubstituted phenyl or trifluoromethyl.

Most preferably X and R combined are methoxy, Ar is phenyl substituted with alkyl or naphthyl substituted with alkoxy, $R_2$, $R_3$, $R_4$ and $R_5$ are hydrogen, methyl or trifluoromethyl.

The catalytic carbonylation of the compound of formula II is conducted at a temperature between about 25° C. and about 200° C., preferably about 50–150° C., and most preferably about 80°–130° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (14.7 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from about 300 to about 3000 psig at the reaction temperature, and most preferred is a pressure from about 500 to about 1,500 psig. It should be noted that the presence of oxygen is undesirable in the carbonylation reaction of this invention. Hence, an atmosphere of 100% carbon monoxide is most preferred to carry out this process. Various inert gases can, however, be incorporated in the reaction mass (nitrogen, argon, etc.) the only criteria being that the process should not be slowed to the point of requiring exceptionally long periods to complete the reaction.

The carbonylation is conducted in the presence of at least about one mol of water per mol of the compound of formula II; however, an excess is preferred in order to assist in driving the reaction to completion. Although there is no real upper limit to the amount of water except that imposed by practicality (e.g. the size of the reaction vessel), an amount up to about 100 mols per mol of the compounds of formula II is useful in the process. Further, controlling the amount of water or of alcohol used in the process of this invention is advantageous in terms of producing the highest yields. Therefore, an amount from about 1 to about 50 mols of water per mol of the compounds of formula II is preferred, and an amount from about 1 to about 10 mols of water per mol of the ether or thioether is most preferred. The product of the reaction is a carboxylic acid (where $R_1$ is H). These compounds have the following formula:

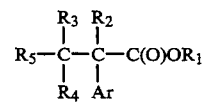

where $R_1$ is hydrogen or alkyl and Ar, $R_2$, $R_3$, $R_4$ and $R_5$ are as previously defined.

In a preferred embodiment of this invention, the carbonylation reaction is initiated under neutral conditions, i.e., with no added acid. It can also be performed in the presence of an added acid. When acids are added, such acids include sulfuric acid, phosphoric acid, sulfonic acids, or acetic or halo- substituted acetic acids. A hydrogen halide acid such as hydrochloric or hydrobromic acid is preferred. The hydrogen halide may be added as a gas phase or as a liquid phase (e.g., in the form of an alcoholic solution). Any concentration may be used. Hydrochloric acid is particularly preferred, at a concentration up to about 10%; more highly preferred is a concentration from about 10% to about 30%.

The catalytic carbonylation process of this invention is conducted in the presence of a reaction-promoting quantity of a) palladium metal or a palladium compound in which the palladium has a valence of 1 or 2 or b) a mixture of i) palladium(O) or a palladium compound in which the palladium has a valence of 1 or 2 and ii) a copper compound having a valence of 1 or 2 with c) at least one acid-stable ligand. Ligands which may be used include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like. In one embodiment, the palladium and copper are added as a pre-formed complex of palladium(II) chloride or bromide, copper(II) chloride or bromide and carbon monoxide or any other similar complex. In a preferred embodiment, active catalytic species are formed in situ (a homogeneous catalyst system) by the addition to the reaction mixture of the individual components, i.e., a ligand, a copper compound, and a palladium compound such as the inorganic salts of palladium(II) and copper-(II) such as the chlorides, bromides, nitrates, sulfates, or acetates. In the most preferred embodiment, triphenylphosphine, and palladium(II) chloride or triphenylphosphine, copper(II) chloride, and palladium(II) chloride are used and are added individually or together, either simultaneously or sequentially.

Palladium and/or copper compounds can be supported on carbon, silica, alumina, zeolite, clay, and other polymeric materials and used as the heterogeneous catalysts (the support is a solvent, insoluble material). Examples of palladium and/or copper support materials and catalysts used in the process of this invention are palladium on carbon, Pd(OH)2 on carbon, Pd(II) exchanged Zeolite LZ-Y62, Pd(II) and Cu(II) exchanged clay montmorillonite KSF.

The amount of palladium compound (salt) in the mixture of copper and palladium compounds (salts) preferably employed is such as to provide from about 4 to about 8000 mols of the compound of formula II per mol of the salt or of mixture of metal salts; more preferred is an amount to provide from about 10 to about 4000 mols of compound of formula II per mol of the salt or salts mixture; the most preferred amounts provide from about 20 to 2000 mols of the compounds of formula II per mol of the metal salt or metal salt mixture. The process of this invention is conducted in the presence of at least one mol of ligand per mol of the salt or mixture of metal salts. More preferably about 2 to about 40 mols of ligand per mol of the salt or the mixed salts are present, and most preferably about 2 to about 20 mols of ligand per mol of salt or mixed salts are used.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; aliphatic or aromatic carboxylic esters, for example, methyl formate, methyl acetate, ethyl acetate, methyl benzoate, and similar compounds; and aromatic hydrocarbons, for example, isobutylbenzene (IBB), toluene, ethyl benzene, xylenes, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is the corresponding ester of the carboxylic acid. Most highly preferred are ketones, especially methyl ethyl ketone. When solvents are used, the amount can be up to about 100 mL per gram of the compounds of formula II, but the process is most advantageously conducted in the presence of about 1 to 30 mL per gram of the compound of formula II.

The following examples are given to illustrate the process of this invention and are not intended as a limitation thereof.

EXAMPLES

MEBB = 1-Methoxy-1-(4'-isobutylphenyl)ethane
IBP = 2-(4'-Isobutylphenyl)propionic acid (ibuprofen)
LA = 3-(4'-isobutylphenyl)propionic acid
CEBB = 1-Chloro-1-(4'-isobutylphenyl)ethane
PME = Methyl 2-(4'-isobutylphenyl)propanoate
LME = Methyl 3-(4'-isobutylphenyl)propanoate
HEBB = 1-Hydroxy-1-(4'-isobutylphenyl)ethane
EIBB = 1-(4'-isobutylphenyl)ethane
IBS = 4-isobutylstyrene

Example 1

A mixture of MEBB (0.96 g, 5 mmol), PdCl$_2$ (18 mg, 0.10 mmol), CuCl$_2$ (50 mg, 0.37 mmol), Ph$_3$P (130 mg, 0.50 mmol), and 10 wt % aqueous hydrochloric acid (5 mL) in methyl ethyl ketone (25 mL) was carbonylated for 4.5 hours at 109°–112° C. under 900 psig of CO.

GC Analysis: IBP (80.8%), LA (9.8%), PME (6.6%), LME (0.8%), MEBB (0.2%), EIBB (0.7%), HEBB (0.5%).

Example 2

The carbonylation was carried out as described in Example 1 with 2 mL of 10 wt% aqueous hydrochloric acid instead of 5 mL.

GC Analysis (after 4 hours): IBP (65.6%), LA (5.6%), PME (12%), LME (0.4%), MEBB (1.3%), EIBB (5.2%), HEBB (0.3%), CEBB (8.4%), and heavies (1.2%).

Example 3

The carbonylation was carried out as described in Example 1 with 5 mL of 20 wt % aqueous hydrochloric acid instead of 10 wt % acid.

GC Analysis (after 3 hours): IBP (84.3%), LA (3.9%), PME (4.0%), LME (0.7%), MEBB (0.5%), EIBB (0.9%), HEBB (1.3%), CEBB (1.4%), and others (3.0%).

Example 4

A mixture of MEBB (0.96 g, 5 mmol), PdCl$_2$ (18 mg, 0.10 mmol), CuCl$_2$ (50 mg, 0.37 mmol), Ph$_3$P (130 mg, 0.50 mmol), and an aqueous solution of saturated boric acid (5 mL) in methyl ethyl keton (30 mL) was carbonylated for 24 hours at 109°–112° C. under psig of CO.

GC Analysis: IBP (67.4%), LA (10.2%), PME (6.1%), LME (2.0%), MEBB (1.3%), HEBB (2.2%), IBS (8.6%), and heavies (1.1

It is obvious that many variations may be made in the products and processes set forth above without departing from the spirit and scope of this invention.

We claim:

1. A process for preparing an aryl-substituted aliphatic carboxylic acid thereof having the formula:

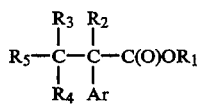

where $R_1$ is hydrogen or alkyl, $R_2$, $R_3$, $R_4$ and $R_5$ are the same or different and are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl which comprises treating a compound of the formula:

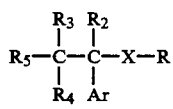

where X is sulfur or oxygen and R is alkyl or aryl either substituted or unsubstituted; Ar, $R_2$, $R_3$, $R_4$ and $R_5$ are as previously defined and water with carbon monoxide at a pressure of at least about 1 atmosphere and a temperature from about 25° C. to about 200° C. in the presence of a catalyst that is a) palladium(O) or a compound of palladium where palladium has a valence of 1 or 2 or b) a mixture of palladium(O) or the compounds of palladium where palladium has a valence of 1 or 2 and the compounds of copper having a valence of 1 or 2 and (c) at least one acid stable ligand.

2. A process of claim 1 wherein the palladium compound is palladium(II) chloride or bromide and the copper compound is copper(I) chloride or copper(II) chloride.

3. A process of claim 1 wherein the amount of palladium compound or mixture of palladium compound and copper compound employed is such as to provide about 4–8000 mols of the compound of formula II per mol of palladium compound or mixture of palladium compound and copper compound.

4. A process of claim 1 wherein X is oxygen.

5. A process of claim 4 wherein R is alkyl.

6. A process of claim 5 wherein X and R combined are methoxy.

7. A process for preparing ibuprofen which comprises carbonylating 1-methoxy-1-(4'-isobutylphenyl)ethane with carbon monoxide in an aqueous acidic medium containing methyl ethyl ketone as a solvent at a temperature in the range of about 50°–150° C. and a carbon monoxide pressure in the range of about 500–1500 psig in the presence of (a) a palladium(II) compound or b) a mixture of a palladium(II) compound and a copper (II) compound and (c) at least one acid-stable monodentate phosphine ligand and in the presence of an amount of hydrogen chloride such as to provide an amount up to about 10 mols of hydrogen chloride per mol of 1-methoxy-1-(4'-isobutylphenyl)ethane.

8. A process of claim 7 wherein the palladium(II) compound is palladium(II) chloride the copper (II) compound is copper(II) chloride and the ligand is triphenylphosphine.

9. A process of claim 7 wherein the palladium compound or the mixture of palladium, copper compounds and the ligand are present in amounts such as to provide about 20–2000 mols of said 1-methoxy-1-(4'-isobutylphenyl)ethane per mol of the palladium compound or the mixture of palladium and copper compounds and about 2–20 mols of ligand per mol of palladium compound or the mixture of palladium and copper compounds.

10. A process of claim 7 wherein the hydrogen chloride is from about 10% (by weight) to about 30% (by weight) HCl.

* * * * *